(12) United States Patent
Adler

(10) Patent No.: US 7,397,941 B1
(45) Date of Patent: Jul. 8, 2008

(54) METHOD AND APPARATUS FOR ELECTRON BEAM INSPECTION OF REPEATED PATTERNS

(75) Inventor: David L. Adler, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 896 days.

(21) Appl. No.: 10/702,800

(22) Filed: Nov. 6, 2003

Related U.S. Application Data

(60) Provisional application No. 60/482,225, filed on Jun. 24, 2003.

(51) Int. Cl.
*G06K 9/00* (2006.01)
(52) U.S. Cl. .................................. 382/151; 382/144
(58) Field of Classification Search ................ 382/141, 382/144, 145, 148, 149, 151
See application file for complete search history.

(56) References Cited

U.S. PATENT DOCUMENTS

| | | | | |
|---|---|---|---|---|
| 4,845,558 | A * | 7/1989 | Tsai et al. ................ | 348/126 |
| 5,513,275 | A * | 4/1996 | Khalaj et al. ............. | 382/149 |
| 5,578,821 | A | 11/1996 | Meisberger et al. | |
| 6,002,810 | A * | 12/1999 | Wakisawa et al. ........ | 382/298 |
| 6,091,846 | A * | 7/2000 | Lin et al. ................ | 382/145 |
| 6,507,417 | B1 * | 1/2003 | Makihira et al. .......... | 358/486 |
| 6,928,185 | B2 * | 8/2005 | Yonezawa ................ | 382/149 |
| 6,946,655 | B2 * | 9/2005 | Almogy et al. ........... | 250/310 |
| 6,973,208 | B2 * | 12/2005 | Kuwabara ................ | 382/145 |
| 7,065,239 | B2 * | 6/2006 | Maayah et al. ........... | 382/145 |
| 2002/0070340 | A1 * | 6/2002 | Veneklasen et al. ....... | 250/310 |
| 2003/0081826 | A1 * | 5/2003 | Karin et al. .............. | 382/151 |

OTHER PUBLICATIONS

Veneklasen, Lee H., "The continuing development of low-energy electron microscopy for characterizing surfaces", Rev. Sci. Instrum, Dec. 1992, pp. 5513-5532, vol. 63, No. 12, American Institute of Physics.

* cited by examiner

*Primary Examiner*—Colin LaRose
(74) *Attorney, Agent, or Firm*—Okamoto & Benedicto LLP

(57) ABSTRACT

One embodiment disclosed relates to a method of detecting defects in a microminiature pattern repeated over a particular surface of an object. The method includes providing an image detector capable of resolving intensity data for each pixel of an array of m×n pixels of an image projected thereupon. An area of the surface of the object is illuminated with incident electrons, radiation from the illuminated area is detected, and image data from the detected radiation is retrieved into a data processor. If necessary, the image data is rotated for alignment purposes. The scale of the image data is then adjusted such that a dimension of a cell of the repeated pattern in the image data is equivalent to a distance across an integer number of pixels of the m×n pixel array. With the scale adjusted, then features in one cell of the repeated pattern are compared with features in another cell of the repeated pattern to detect said defects.

5 Claims, 7 Drawing Sheets

METHOD AND APPARATUS FOR ELECTRON BEAM INSPECTION OF REPEATED PATTERNS

CROSS-REFERENCE TO RELATED APPLICATIONS

The present application claims the benefit of provisional patent application No. 60/482,225, filed Jun. 24, 2003, entitled "Method and Apparatus for Electron Beam Inspection of Repeated Patterns", by inventor David L. Adler, the disclosure of which is hereby incorporated by reference.

BACKGROUND OF THE INVENTION

1. Field of the Invention

The present invention relates to electron beam inspection methods and apparatus.

2. Description of the Background Art

A variety of methods have been used to examine microscopic surface structures of semiconductors. These have important applications in the field of semiconductor chip fabrication, where microscopic defects at a surface layer can make the difference between a properly functioning or non-functioning IC. For example, holes or vias in an intermediate insulating layer often provide a physical conduit for an electrical connection between two outer conducting layers. If one of these holes or vias becomes clogged with non-conductive material, this electrical connection between layers will not be established.

Automated inspection of the semiconductors is used to ensure a level of quality control in the manufacture of the integrated circuits. It is desirable to improve the collection, processing, and analysis of image obtained during the automated inspection of manufactured substrates, such as semiconductor wafers, photomask reticles, flat panel screens, and the surfaces of other objects.

SUMMARY

One embodiment of the invention pertains to a method of detecting defects in a microminiature pattern repeated over a particular surface of an object. The method includes providing an image detector capable of resolving intensity data for each pixel of an array of m×n pixels of an image projected thereupon. An area of the surface of the object is illuminated with incident electrons, radiation from the illuminated area is detected, and image data from the detected radiation is retrieved into a data processor. If necessary, the image data is rotated for alignment purposes. The scale of the image data is then adjusted such that a dimension of a cell of the repeated pattern in the image data is equivalent to a distance across an integer number of pixels of the m×n pixel array. With the scale adjusted, then features in one cell of the repeated pattern are compared with features in another cell of the repeated pattern to detect said defects.

Another embodiment of the invention pertains to a method of electron beam inspection of a substrate having an array of repeated cells thereon. A first portion of the array is illuminated with a beam of electrons, a first image is generated by imaging electrons mirrored from the first portion, and an extent of a sub-pixel difference between a cell within the first portion and a nearest integer number of pixels is determined. Similarly, a plurality of other portions of the array is illuminated. The first image derived from the first portion is compared to a second image derived from one of the other portions, wherein the second image is selected such that a similar sub-pixel difference exists between a cell within the other array portion and the nearest integer number of pixels.

Another embodiment of the invention pertains to an apparatus for electron beam inspection of a substrate having an array of repeated cells thereon. The apparatus includes at least a low energy electron microscope column, an array detector, and a data processor. The low energy electron microscope column includes mirror mode for imaging a substrate surface. The array detector is used to collect image data derived from the LEEM column. The data processor is used for retrieving and processing the image data. The data processor includes software components including at least an image rotator, a period adjuster, and an image comparator. The period adjuster is utilized to adjusting scale of the image data such that a dimension of a cell of the repeated pattern in the image data is equivalent to a distance across an integer number of pixels.

DETAILED DESCRIPTION

Figure 1:
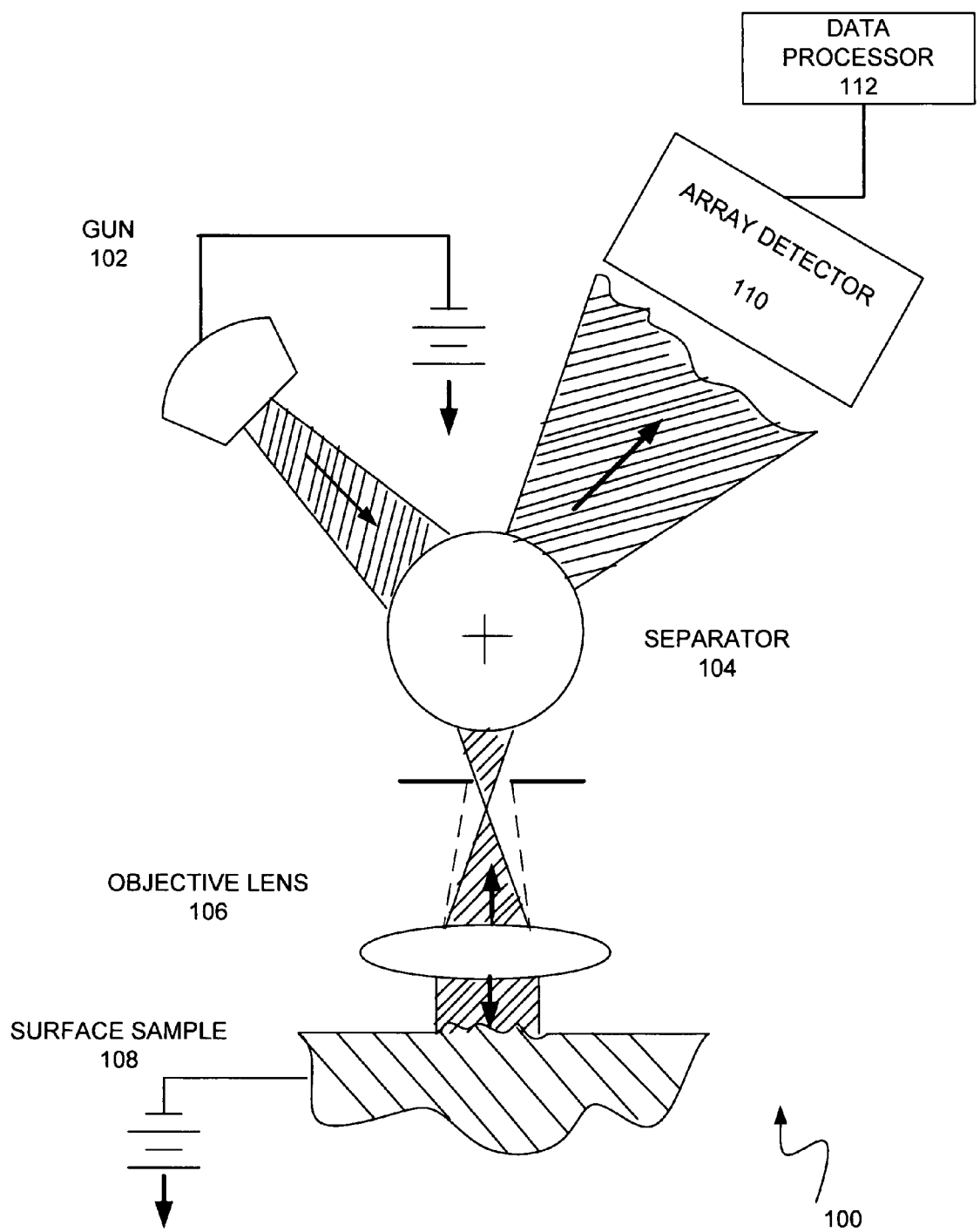
FIG. 1 is a schematic diagram depicting an electron beam apparatus for detecting defects in objects with repeated surface patterns in accordance with an embodiment of the invention.

FIG. 1 is a schematic diagram depicting an electron beam apparatus 100 for detecting defects in objects with repeated surface patterns in accordance with an embodiment of the invention. The electron beam apparatus 100 is shown as including a low-energy electron microscope (LEEM). The elements depicted include an electron gun 102, a beam separator 104, an objective lens 106, a surface of a sample substrate 108, an array detector 110, and a data processor 112.

The electron gun 102 supplies electrons that illuminate the sample or regions thereof. Absorption, scattering, and interference of electrons at the sample allow observation of detail much smaller than a light optical microscope can resolve. A characteristic feature of the LEEM is the beam separator 104. This element allows the electron illumination and image beams to fold back upon themselves after reflecting from the surface 108 of the substrate. The objective lens 106 acts upon incoming illumination and outgoing image beams in very similar ways, but above the objective lens 106, a magnetic prism or other beam separator 104 deflects the beams in opposite directions, creating separate spaces or the illumination and imaging electron optics. The array detector 110 receives the electrons for imaging and generates image data therefrom. The array detector 110 may utilize, for example, an array of charge-coupled devices. In one embodiment, the array detector 110 may comprise a time delay integration detector which may be used, for example, to collect image data from moving semiconductor wafers. The data processor 112 retrieves and processes the image data from the array detector 110.

Figure 2:
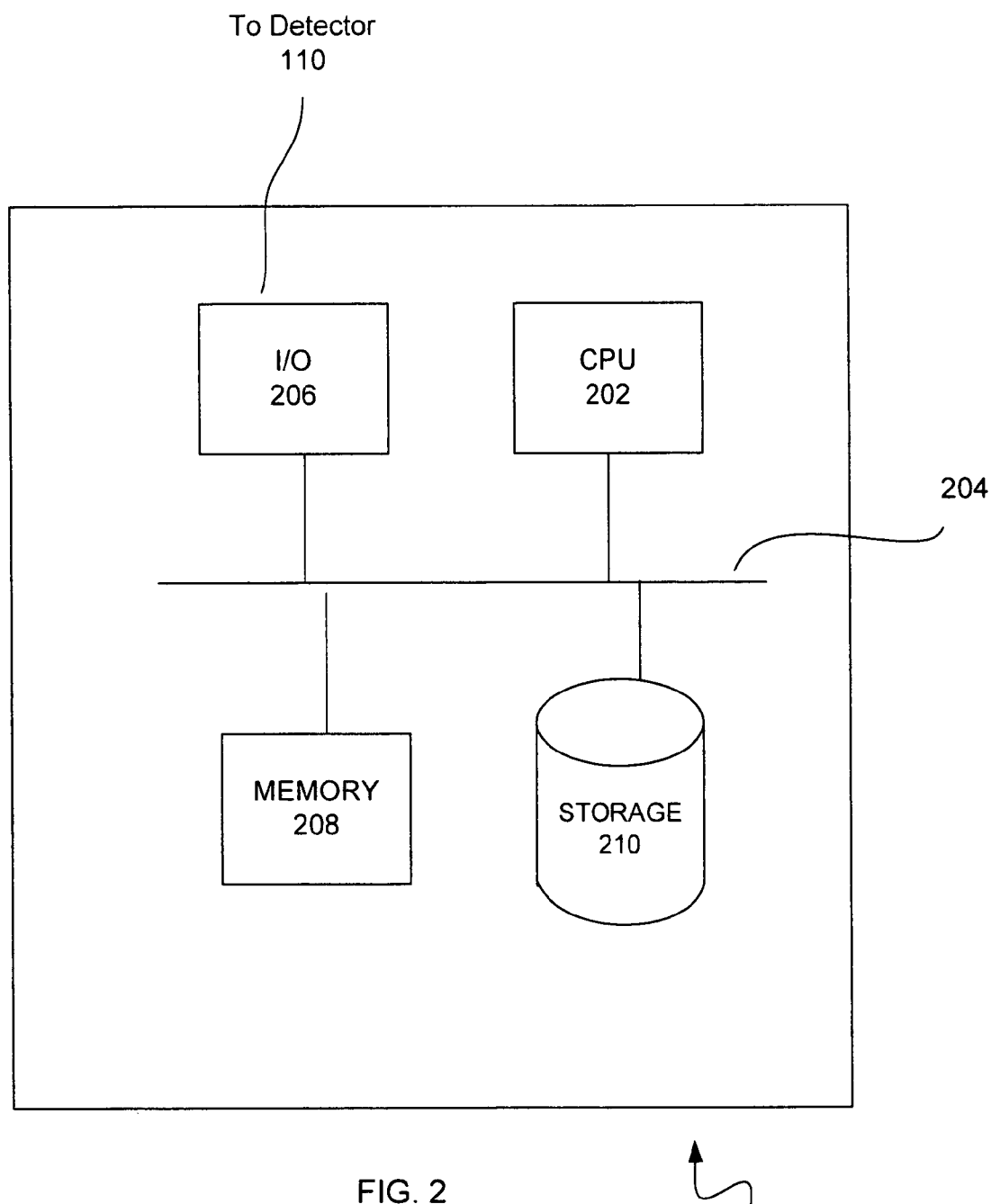
FIG. 2 is a block diagram depicting the data processor for the electron beam apparatus in accordance with an embodiment of the invention.

FIG. 2 is a block diagram depicting the data processor 112 for the electron beam apparatus in accordance with an embodiment of the invention. The data processor 112 includes a central processor unit (CPU) 202, a communications system 204, an input/output (I/O) interface 206, a memory 208, and data storage 210.

The CPU 202 may comprise a microprocessor with local memory. The CPU 202 functions as the controller for the data processor 112 and may also perform the computing operations within the data processor 112. Other embodiments may utilize separate image processors to rapidly process the image data. The communications system 204 may comprise one or more buses to enable the components within the data processor 112 to communicate with each other.

Image data from the array detector 110 may be received by the data processor 112 by way of the I/O interface 206. The I/O interface 206 may comprise, for example, one of the various standard computer interfaces available commercially. Software components, image data, and other data may be stored in memory 208 and data storage 210. The memory 208 may comprise forms of semiconductor memory, including, for example, static random access memory (SRAM) and/or dynamic random access memory (DRAM). The storage 210 may comprise a hard disk drive or other form of data storage.

Figure 3:
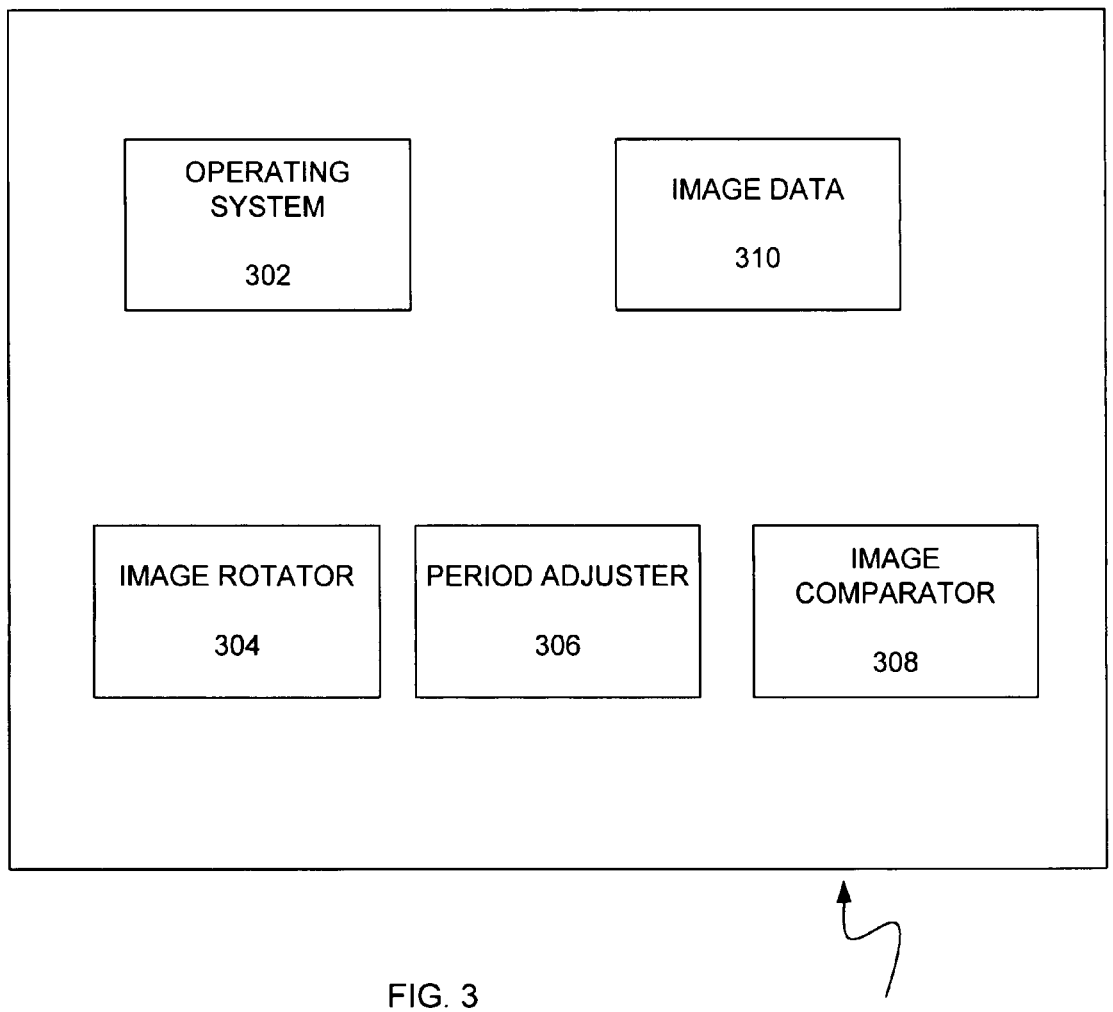
FIG. 3 is a block diagram depicting software components and data within the memory of the data processor in accordance with an embodiment of the invention.

FIG. 3 is a block diagram depicting software components and data within the memory 208 and/or storage 210 of the data processor 210 in accordance with an embodiment of the invention. The software components include an operating system 302, an image rotator 304, a period adjuster 306, and an image comparator 308. The data includes image data 310 received from the detector 110.

The operating system 302 provides device drivers and other basic software functions for the data processor 112. The image rotator 304 comprises a software module that operates on image data to rotate an image. The period adjuster 306 comprises a software module that operates on image data to change the scale of image data with respect to one or both dimensions. The image comparator 308 comprises a software module that compares two sets of image data. Such a comparison may be utilized in detecting defects in accordance with an embodiment of the invention.

Figure 4:
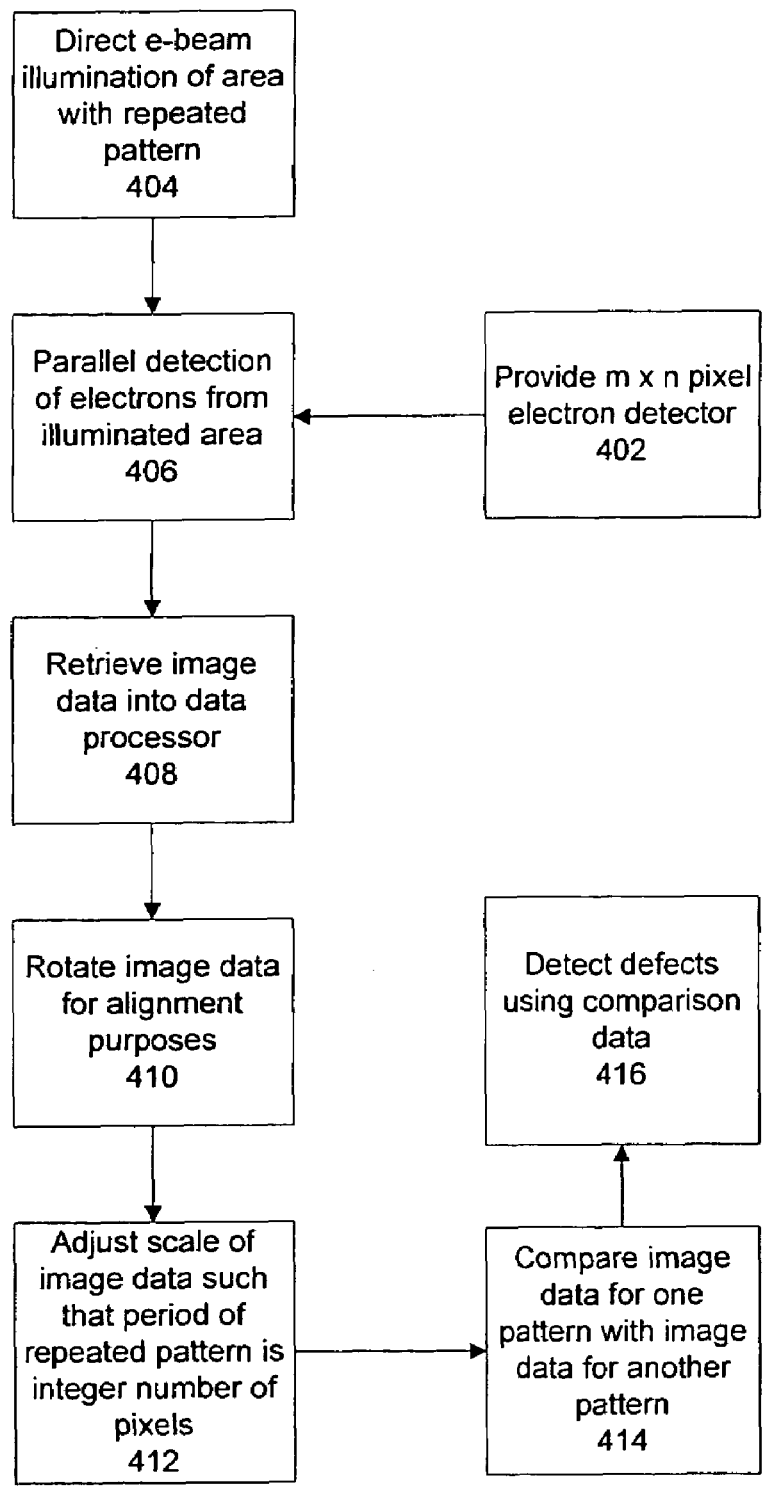
FIG. 4 is a flow chart depicting a first method of detecting defects in a microminiature pattern repeated over a particular surface area of an object in accordance with an embodiment of the invention.

FIG. 4 is a flow chart depicting a first method 400 of detecting defects in a microminiature pattern repeated over a particular surface area of an object in accordance with an embodiment of the invention. For example, this method 400 may be applied to detect defects in repeated cells on a semiconductor substrate, such as for a memory array, or in a reticle mask, or other similar surface. A preliminary step 402 comprises providing an m×n pixel array electron detector 112.

An area of the specimen surface including a repeated pattern is illuminated directly 404 with an electron beam. Such direct illumination may be accomplished, for example, using a LEEM column, such as the one discussed above in relation to FIG. 1. The direct illumination is advantageous in that image data may be collected more rapidly with direct illumination, rather than by scanning the electron beam across the surface. In mirror mode of the LEEM, electrons are mirrored off of the illuminated surface area. The mirrored electrons travel back up the column and are separated from the incident electrons by the beam separator 104. The mirrored electrons are detected in parallel 406 using the array detector 110, and the image data is retrieved 408 from the detector 110 into the data processor 112.

If necessary, the image data may be rotated 410 to align rectilinear cells of the repeated pattern along the x and y axes of the pixel array. The rotation of the image may be performed by the image rotator 304 software module processing the image data in memory 208 of the data processor 112. After such alignment, a rectangular cell of the repeated pattern should be in rotational alignment with the rows and columns of image pixels.

The scale of the image data is then adjusted 412. The scale adjustment 412 is performed such that the period of the repeated pattern is an integer number of pixels in both the x and y (i.e. row and column) dimensions. In other words, after the scaling, a rectangular cell of the repeated pattern should have be an integer number of pixels wide and an integer number of pixels long. The scaling operations would typically utilize some form of interpolation algorithm.

Once the image data is rotationally aligned 410 and adjusted in scale 412 as described above, feature in the image data from one cell (i.e. one pattern of the repeated pattern) is compared 414 with features in the image data from another cell (i.e. another pattern of the repeated pattern). Using the comparison data, defects in one or the other cell may be detected 416. For example, if a first cell is known or assumed to be effectively without defect, then the difference in the image data between the first cell and a second cell is indicative of whether the second cell is defective or not.

Figure 5:
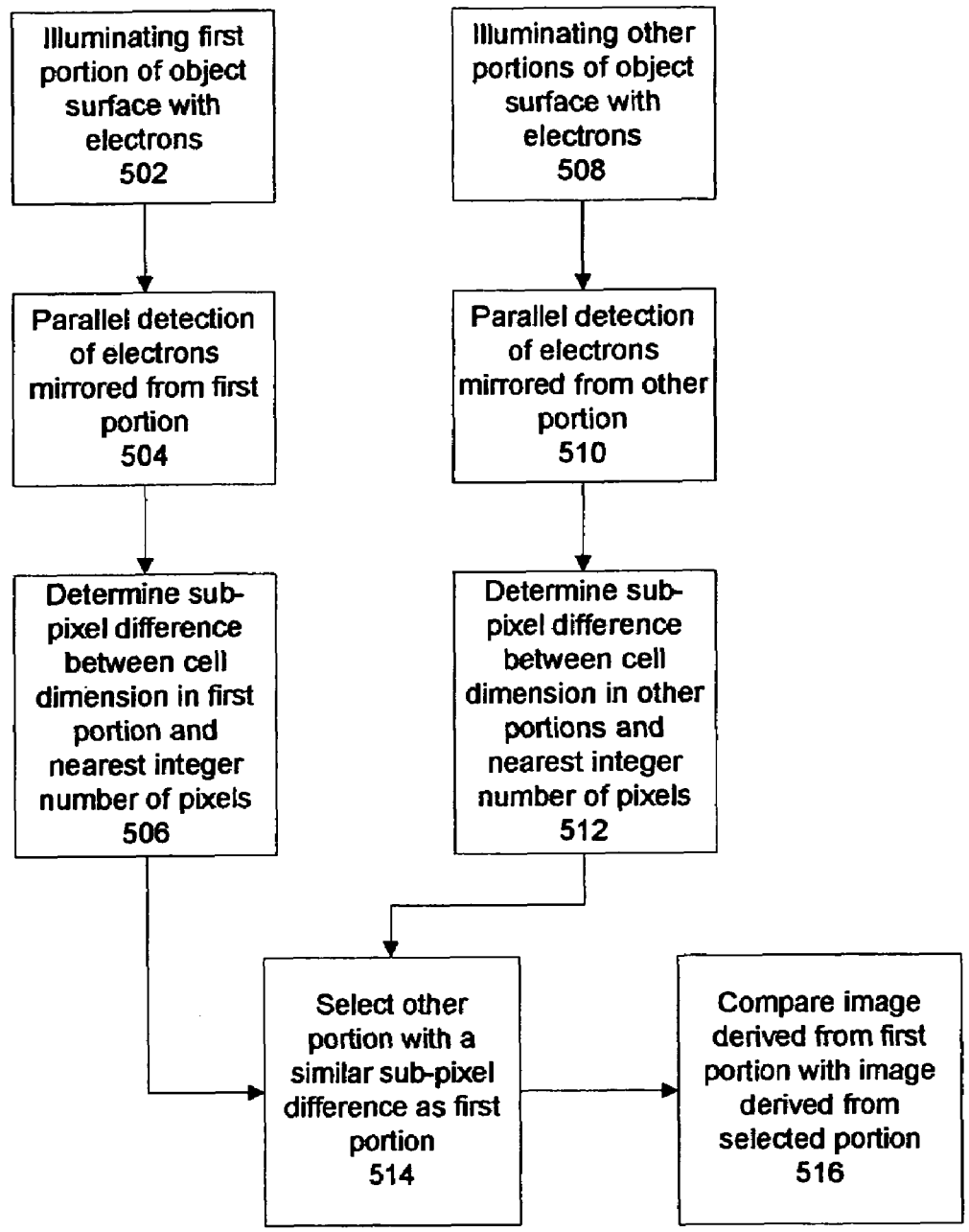
FIG. 5 is a flow chart depicting a second method of detecting defects in a microminiature pattern repeated over a particular surface area of an object in accordance with an embodiment of the invention.

FIG. 5 is a flow chart depicting a second method 500 of detecting defects in a microminiature pattern repeated over a particular surface area of an object in accordance with an embodiment of the invention. This method 500 may also be applied, for example, to detect defects in repeated cells of a semiconductor substrate being manufactured, or in a reticle mask, or other similar surface.

A first portion of the object surface is illuminated 502 with electrons. For example, the LEEM column depicted in FIG. 1 may be used for direct illumination with low-energy electrons. If the LEEM is in mirror mode, then the low-energy electrons incident on the surface are mirrored back up through the column. After beam separation, the mirrored electrons are parallel detected 504 using an array detector 110.

Optionally, the collected image data may be rotated to align the repeated pattern to the rows and columns of the pixel array. However, in some configurations, such rotational alignment may be unnecessary since the pattern may already be aligned to the pixel rows and columns. Next, a sub-pixel difference may be determined 506 between cell dimensions in said first portion and the nearest integer number of pixels.

Similarly, other portions of the object surface are also illuminated 508 with electrons. After beam separation, the mirrored electrons are parallel detected 510 using the array detector 110, and a sub-pixel difference may be determined 512 between cell dimensions in each said other portion and the nearest integer number of pixels. Note that the illumination, detection, and determination for these other portions may each be performed together with the analogous step for first portion (although FIG. 5 shows them as being performed separately in parallel).

One of the other portions with a similar (or the same) sub-pixel difference as said first portion is then selected 514. Since the sub-pixel difference is similar, the selected portion and the first portion are advantageously comparable with each other. Hence, the image data derived from the first portion is compared 516 with the image data derived from the selected portion. The comparison data may then be used in detecting defects in one or the other portions.

Figure 6:
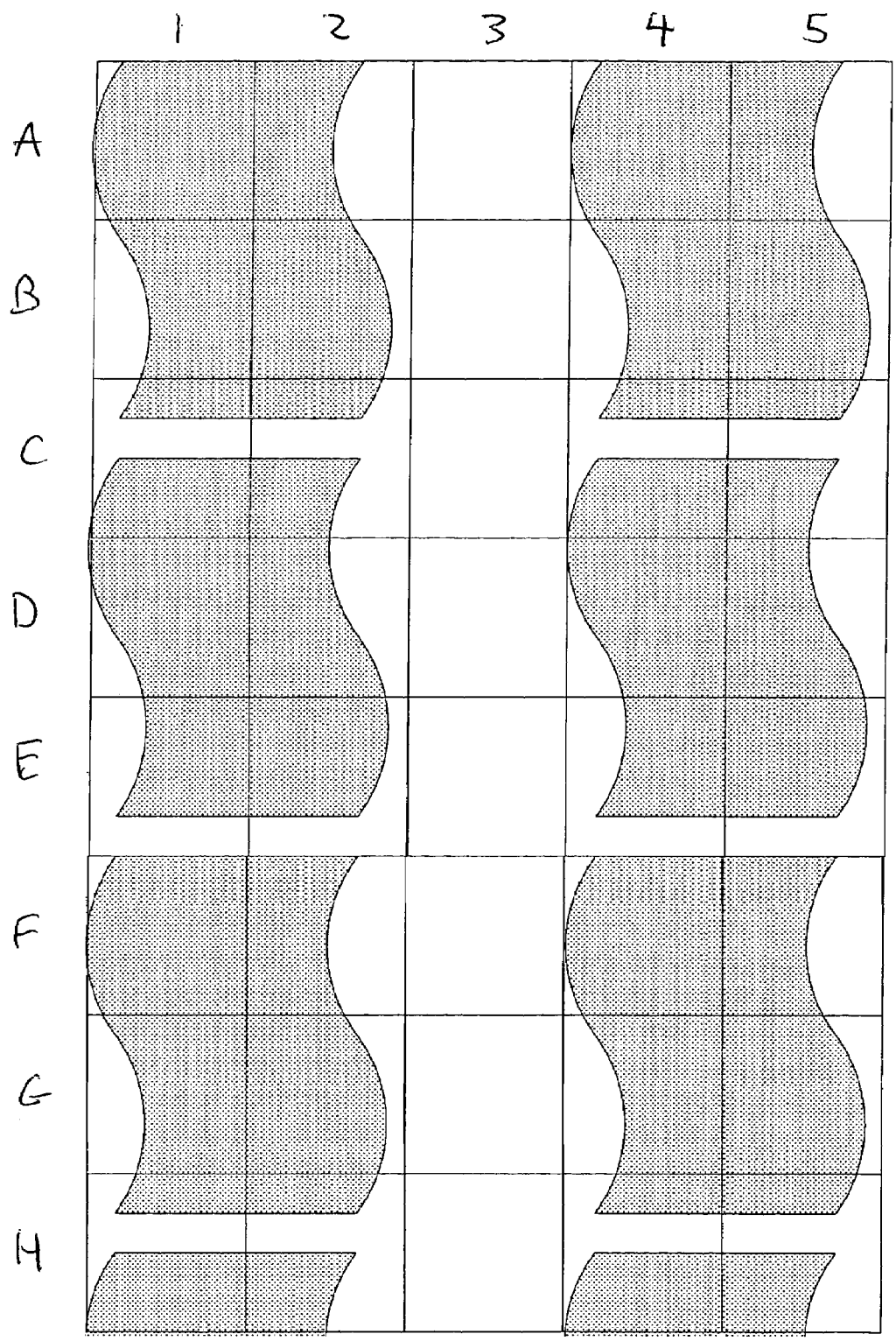
FIG. 6 is a diagram showing a repeated pattern overlaying an array of pixels to illustrate a cell with a non-integer pixel dimension.

FIG. 6 is a diagram showing a repeated pattern overlaying an array of pixels to illustrate a cell with a non-integer pixel dimension. The rows of pixels are labeled A, B, C, D, and so on, while the columns of pixels are labeled 1, 2, 3, 4, and so on. Hence, the first row of pixels in FIG. 6 are designated A1, A2, A3, A4, etc. The second row of pixels are designated B1, B2, B3, B4, etc. And so on.

As shown in FIG. 6, a cell (or pattern) of the repeated pattern is three pixels wide (horizontally) and two and a half pixels long (vertically). For example, a first cell in the upper left corner may be considered as covering entire pixels A1, A2, A3, B1, B2, and B3, and the top half of pixels C1, C2, and C3. Hence, in this example, the cell is an integer number of pixels wide in the horizontal or X dimension, but is not an integer number of pixels long in the vertical or Y dimension. This is disadvantageous in that two cells are not necessarily comparable by comparing the pixel data directly. For example, a second cell below the first cell covers the bottom half of pixels C1, C2, and C3, and entire pixels D1, D2, D3, E1, E2, and E3. Comparing the image data pixel-by-pixel between the first and the second cells would not be particularly meaningful because the fractional pixel Y-dimension of each cell. This disadvantage may be overcome by adjusting 412 the scale of the image data in the Y-dimension per the method 400 of FIG. 4.

Figure 7:
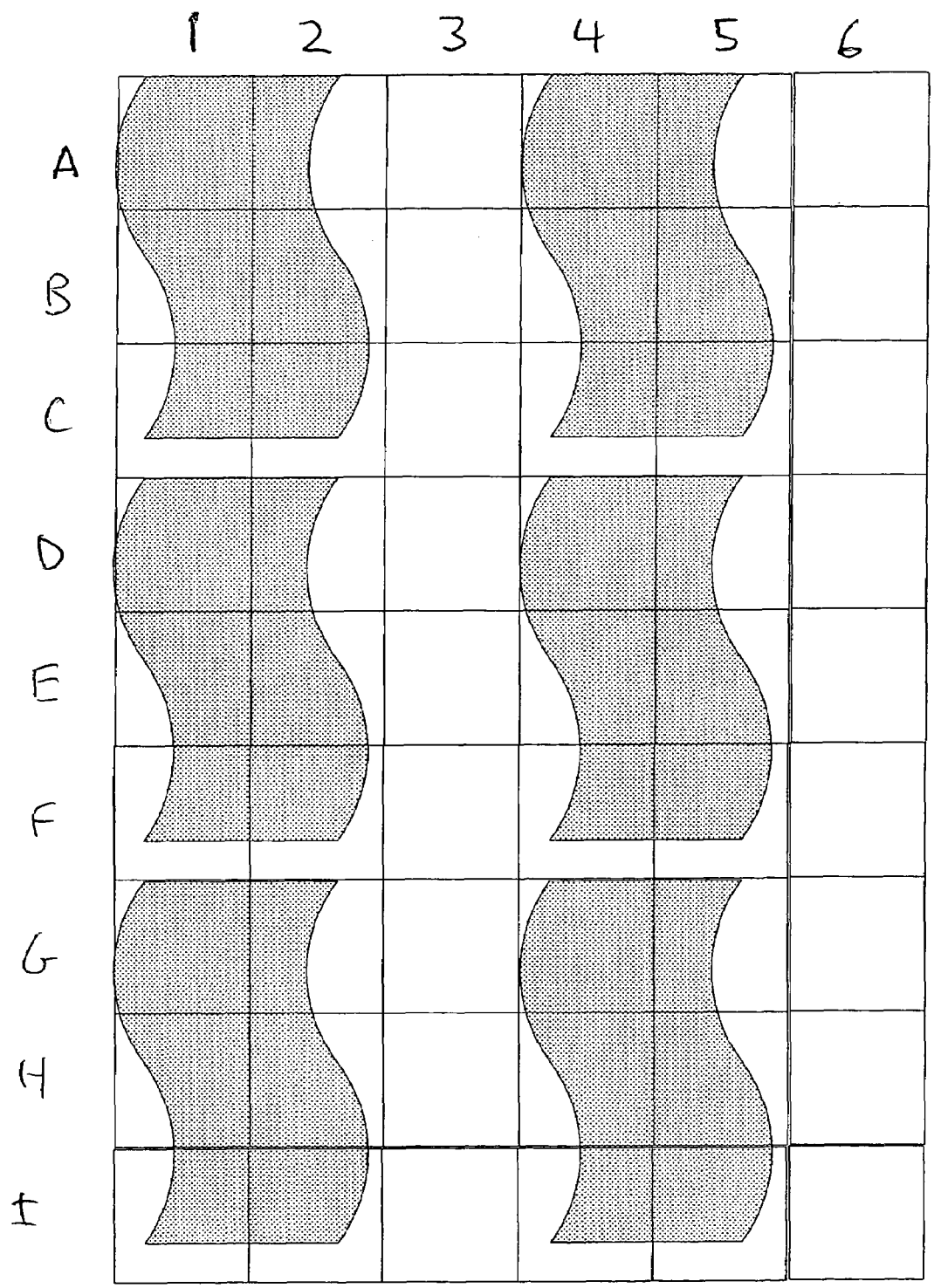
FIG. 7 is a diagram showing the repeated pattern of FIG. 6 after scaling such that each cell has integer pixel dimensions.

FIG. 7 is a diagram showing the repeated pattern of FIG. 6 after scaling such that each cell has integer pixel dimensions. In comparison to FIG. 6, the image data shown in FIG. 7 has been adjusted 412 in scale in the vertical or Y dimension per the method 400 of FIG. 4. In other words, the image data has been "stretched" in the Y dimension such that each cell is now three pixels long. Each cell now covers an area that is three pixels wide and three pixels long. For example, the first cell in the upper left corner now covers the entire pixels A1, A2, A3, B1, B2, B3, C1, C2, and C3. With such scaling to make the period of the repeated pattern be an integer number of pixels in both dimensions, the image data from one cell can now be advantageously compared 414 with the image data from another cell. Such comparison data is meaningful and may be used to detect 416 defects in the repeated pattern.

Of course, for ease of explanation, the diagrams in FIGS. 6 and 7 are simplified in that a simplistic pattern is shown, and each cell is shown as covering a small area of just a few pixels. In practice, the patterns would typically be more complex and may be more rectilinear, for example, in a semiconductor memory being manufactured. In addition, each cell would cover a much larger number of pixels. Moreover, both dimensions of a cell would typically not be an integer number of pixels, and so typically both dimensions would need to be scaled. The sub-pixel difference between a cell dimension and an integer number of pixels is also unlikely to be exactly one half of a pixel.

Referring back to FIG. 6, although not every two cells may be meaningfully compared pixel-by-pixel due to the sub-pixel period in the vertical dimension, nevertheless intelligently selected portions of the repeated pattern may be usefully compared pixel-by-pixel.

For example, consider portions where each portion includes two rows of pixels. For instance, a first portion may include pixel rows A, B, and C. A second portion may include pixel rows C, D, and E. A third portion may include pixels rows F, G, and H. And so on for various other portions. The portions may or may not overlap.

Per the method 500 of FIG. 5, it may be determined (506 and 512) that cells of the repeated pattern in the first and third portions have a similar sub-pixel difference in their dimensions. Hence, the image data derived from the third portion may be selected 514 for comparison 516 with the image data derived from the first portion. Note that the portions need not be rows or columns and may comprise other subsets of the image pixels.

The above-described diagrams are not necessarily to scale and are intended be illustrative and not limiting to a particular implementation. The above-described invention may be used in an automatic inspection or review system and applied to the inspection or review of wafers, X-ray masks and similar substrates in a production environment. While it is expected that the predominant use of the invention will be for the inspection or review of wafers, optical masks, X-ray masks, and the like, the techniques disclosed here may be applicable to the high speed electron beam imaging of other substrates with repeated patterns.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of detecting defects in a microminiature pattern repeated over a particular surface of an object, the method comprising:

illuminating a surface of the object with incident electrons;
  deflecting image electrons mirrored from the surface and the incident electrons in opposite directions using a beam separator;
  detecting the image electrons from the surface in parallel using a pixel array electron detector capable of resolving intensity data for each pixel of an image projected thereupon;
  retrieving image data from the detected image electrons from the surface into a data processor;
  determining a sub-pixel difference between a cell dimension in a first portion of the surface and a nearest integer number of pixels;
  determining sub-pixel differences between a cell dimension in other portions of the surface and a nearest integer number of pixels;
  selecting one of the other portions having a sub-pixel difference which is close to the sub-pixel difference in the first portion; and
  comparing features in the first portion with features in said selected portion to detect said defects.

2. The method of claim 1, further comprising performing a scale adjustment utilizing an interpolation algorithm.

3. The method of claim 1, wherein the pixel array electron detector utilizes an array of charge-coupled devices.

4. The method of claim 1, wherein the microminiature pattern comprises a memory cell of a semiconductor memory array.

5. A system for detecting defects in a microminiature pattern repeated over a particular surface of an object, the system comprising:

means for illuminating a surface of the object with incident electrons;

means for deflecting in opposite directions the incident electrons and reflected electrons from the surface;

pixel array electron detection means for detecting the reflected electrons from the illuminated area, wherein the pixel array electron detection means comprises an image detector capable of parallel detection and resolving intensity data for each pixel of an image projected thereupon;

means for retrieving image data from the pixel array electron detection means into a data processor;

means for determining a sub-pixel difference between a cell dimension in a first portion of the surface and a nearest integer number of pixels;

means for determining sub-pixel differences between a cell dimension in other portions of the surface and a nearest integer number of pixels;

means for selecting one of the other portions having a sub-pixel difference which is close to the sub-pixel difference in the first portion; and means for comparing features in the first portion with features in said selected portion to detect said defects.

* * * * *